United States Patent
Gong et al.

(10) Patent No.: US 12,318,786 B2
(45) Date of Patent: Jun. 3, 2025

(54) APPARATUS FOR POLYMERASE CHAIN REACTION OF NUCLEIC ACID

(71) Applicant: STAR ARRAY PTE LTD, Singapore (SG)

(72) Inventors: Haiqing Gong, Singapore (SG); Xudong Zeng, Singapore (SG)

(73) Assignee: STAR ARRAY PTE LTD, Singapore (SG)

( * ) Notice: Subject to any disclaimer, the term of this patent is extended or adjusted under 35 U.S.C. 154(b) by 764 days.

(21) Appl. No.: 17/639,598

(22) PCT Filed: Jul. 15, 2020

(86) PCT No.: PCT/SG2020/050410
§ 371 (c)(1),
(2) Date: Mar. 2, 2022

(87) PCT Pub. No.: WO2021/050002
PCT Pub. Date: Mar. 18, 2021

(65) Prior Publication Data
US 2022/0323964 A1     Oct. 13, 2022

(30) Foreign Application Priority Data
Sep. 9, 2019   (SG) .......................... 10201908290R

(51) Int. Cl.
*B01L 7/02*     (2006.01)
*B01L 7/00*     (2006.01)
*C12Q 1/686*   (2018.01)

(52) U.S. Cl.
CPC ............. *B01L 7/525* (2013.01); *B01L 7/02* (2013.01); *C12Q 1/686* (2013.01)

(58) Field of Classification Search
CPC . B01L 7/525; B01L 7/02; B01L 13/02; C12Q 1/686
USPC ........................................... 422/138
See application file for complete search history.

(56) References Cited

U.S. PATENT DOCUMENTS

2018/0051244 A1   2/2018  Perlman
2019/0091694 A1*  3/2019  Gong ............... C12Q 1/686

FOREIGN PATENT DOCUMENTS

| CN | 206587811 U | * | 10/2017 |
| EP | 2535427 A2 | | 12/2012 |
| LU | 100862 B1 | | 12/2018 |
| WO | 2017213589 A1 | | 12/2017 |
| WO | 2017213592 A1 | | 12/2017 |

\* cited by examiner

*Primary Examiner* — Huy Tram Nguyen
(74) *Attorney, Agent, or Firm* — Bayramoglu Law Offices LLC

(57) ABSTRACT

Thermal cycling apparatus for polymerase chain reaction (PCR) of nucleic acid is provided. Bath media in a first bath and a second bath are maintainable at two different temperatures. A transfer means allows the reactor to be in the two baths in a plurality of thermal cycles to alternately attain a predetermined high target temperature $T_{HT}$ and a predetermined low target temperature $T_{LT}$. A florescent imaging means images the reaction material during the thermal cycling. A powder-cleaning device mechanically removes particles of powder that adhere to the reactor, when powder is the bath medium in use in at least one of the baths.

20 Claims, 13 Drawing Sheets

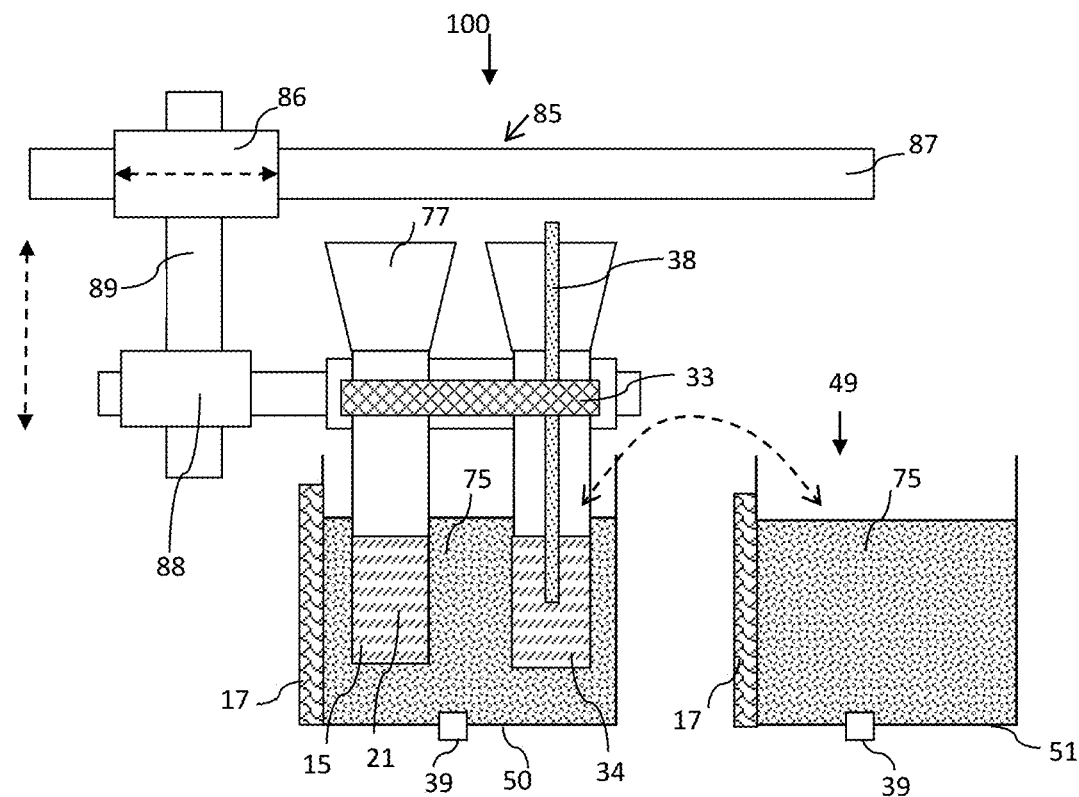
FIG. 1A-PRIOR ART
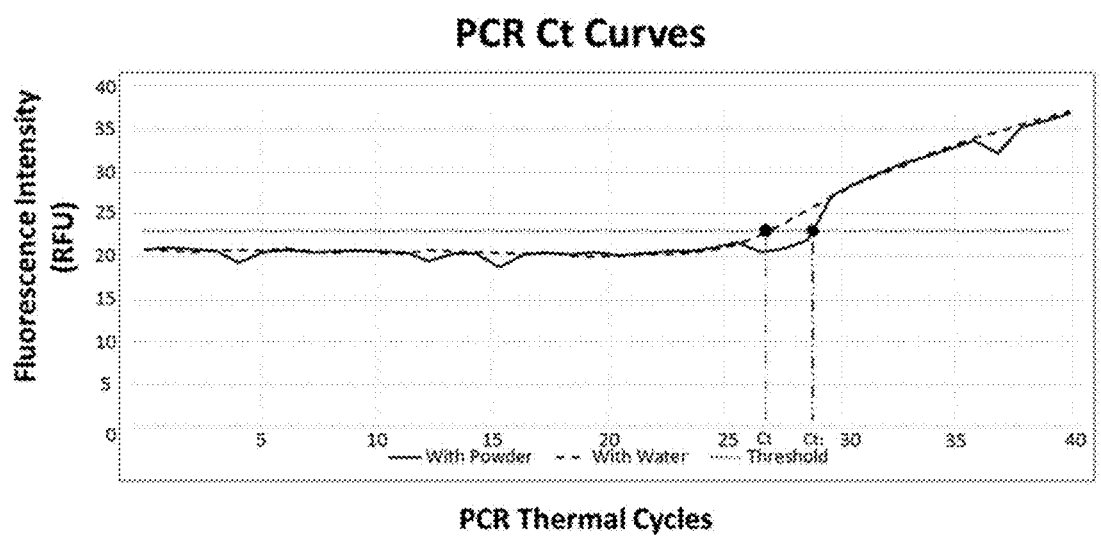
FIG. 1B-PRIOR ART

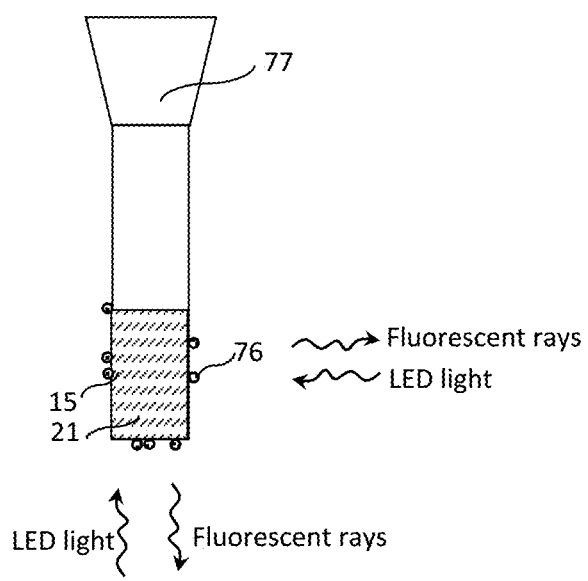
FIG. 2- Proposed Theory

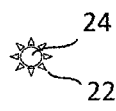 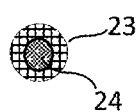 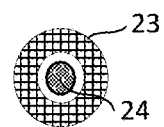
FIG. 4A          FIG. 4B          FIG. 4C
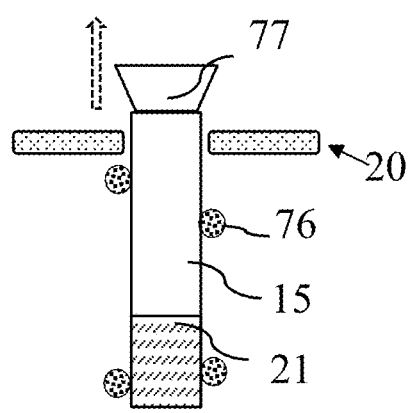 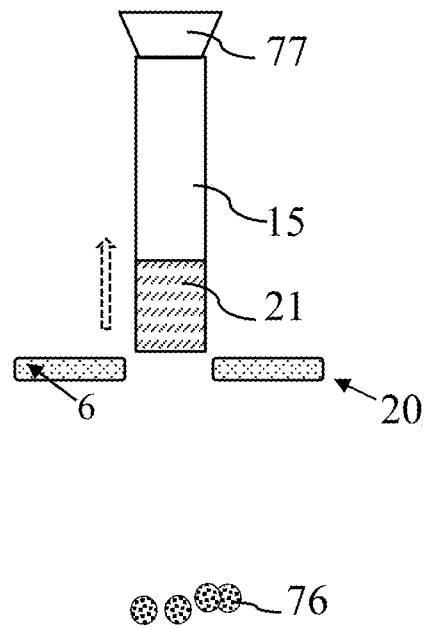
FIG. 5A          FIG. 5B
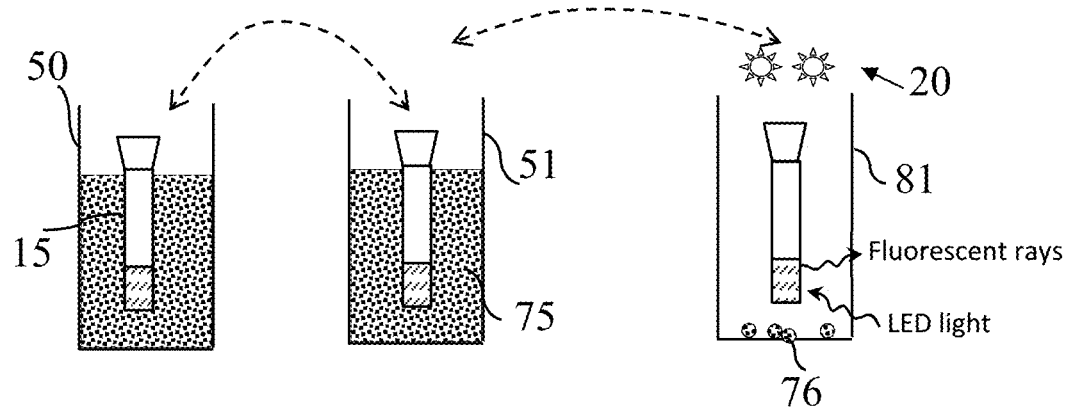
FIG. 6A

APPARATUS FOR POLYMERASE CHAIN REACTION OF NUCLEIC ACID

This application is the national phase entry of International Application No. PCT/SG2020/050410, filed on Jul. 15, 2020, which is based upon and claims priority to Singaporean Patent Application No. 10201908290R, filed on Sep. 9, 2019, the entire contents of which are incorporated herein by reference.

TECHNICAL FIELD

The present invention relates to an apparatus for performing polymerase chain reaction (PCR) of nucleic acid.

BACKGROUND

Polymerase chain reaction (PCR) is increasingly important to molecular biology, food safety and environmental monitoring. A large number of biological researchers use PCR in their work on nucleic acid analyses, due to its high sensitivity and specificity. The PCR is typically conducted by thermal cycling process that is adapted to heat and cool reactors containing the reaction material to different temperatures for DNA denaturation, annealing and extension. Typically, the thermal cycling apparatus employs moving the reactors between two heating baths whose temperatures are set at the target temperatures as required for nucleic acid amplification reactions.

Heating devices in the form of solid metallic blocks are known to be used in place of the heating baths. The solid blocks being designed with cavities to receive the reactors are also known when the reactors are in the shape of capillaries or tubes. However, during a thermal cycling operation, the contact between the reactors containing the biological sample and the solid blocks often fail to be tight enough for a good rate of heat exchange. The traditional water bath PCR cyclers utilize the high thermal conductivity and the high heat capacity of water to achieve efficient heating and cooling. Such cyclers have heating baths containing a volume of water in each as the bath medium. The issue of poor contact as described in the preceding paragraph is automatically addressed with the water bath medium.

The patent application no: PCT/SG2017/050288 teaches use of high thermal conductivity powder as the bath medium. With respect to the liquid bath medium, the high thermal conductivity powder enhances the conductive heat exchange with the reactor(s), homogenizes the temperature field inside a bath and improves temperature uniformity along the reactors. The initial heating time of the baths to the predetermined temperatures is also significantly reduced. The powder also eliminates the issue of liquid adhesion to the surfaces of the reactors when the reactors move between the baths, thereby causing undesirable local drifts in the temperatures of the baths and their calibrations. Such liquid adhesion also undesirably causes the reactors to retain the bath temperature for a duration even after being taken out of the bath. This can be avoided with the powder. The undesirable splashes when the reactor(s) are inserted in the liquid bath media are significantly reduced with the powder. Besides, the powder does not vaporize with time or usage, thereby requiring no refill as in the case of liquids. FIG. 1A shows a schematic view of a portion of a typical thermal cycling apparatus for PCR or other enzymatic reactions to amplify nucleic acids or a fragment of nucleic acid. The two baths 50 and 51 contain powder 76 as the bath medium 75. The bath heater 17 and a bath temperature sensor 39 mounted along the bath surface enable control of the temperature of the bath medium 75. The bath 50 and 51 are open to the ambient only at the top open side 49. The bath 50 may be set at a temperature that is suitable for the step of denaturation and the bath 51 may be set at a temperature that is suitable for the step of annealing and/or extension. The reactor 15 is sealed with a sealant or a cap 77 to block the vapor generated from the reaction material 21 from leaking out. The reactor holder 33 accommodates a plurality of reactors 15. The reactor transfer mechanism 85 transfers the reactors 15 at high speed between the baths 50 and 51 from the top open side 49 as shown by the curved line with double headed arrows to expose them alternately to the different temperatures in the baths 50 and 51 as required for the thermal cycling. Within the reactor transfer mechanism 85, the X stage 86 moves along an X axis linear guide 87 as shown by the dashed horizontal double headed arrow and the Z stage 88 moves along a Z axis linear guide 89 as shown by the dashed vertical double headed arrow. A temperature monitoring unit 34 with a fast response temperature sensor 38 inside is installed on the reactor holder 33 and moves along with the reactor 15 between the baths 50, 51.

In a real-time PCR assay, a positive reaction is detected by accumulation of a fluorescent signal. Fluorescence imaging is typically conducted multiple times or after every thermal cycle to record the progressive change in the reaction material 21. This progressive change is typically plotted as in the PCR Ct (cycle threshold) curve to derive the Ct value where the fluorescence intensity as emitted by the reaction material 21 intersects a predefined threshold level. The derived value of Ct is defined as the number of cycles required for the fluorescent signal to cross the threshold level. Ct values are inversely proportional to the amount of the target nucleic acid in the sample or reaction material 21. Lower the Ct value, greater is the amount of the target nucleic acid in the sample or reaction material 21.

For a rapid PCR, commonly thin and long capillary reactors 15 are used where the reaction material 21 remains at the bottom. When the LED illumination and imaging is from the top of the reactor 15, the LED light from the imaging system is difficult to reach the bottom and the fluorescent rays from the reaction material 21 are difficult to reach the detector outside the reactor 15. Thus, imaging from the side or the bottom of the reactors 15 is preferred.

When powder 76 is used as the bath medium 75, the fluorescence imaging of the nucleic acid needs to be conducted when the reactors 15 are outside the baths 50, 51 as the powder bath-medium 75 is non-transparent to the lights for imaging.

Though the advantages of using the powder 76 as the bath medium 75 are significant, the inventors in this application have established that using powder 76 as the bath medium 75 sometimes appears to result in unreliable PCR Ct values. The same reaction material 21 in different reactors 15 appears to show inconsistent PCR Ct values. FIG. 1B shows the PCR Ct curves over 40 thermal cycles, with the fluorescence intensity recorded after each cycle for the same reactor 15. The solid line represents measured values with the powder 76 as the bath medium 75. The dashed line represents measured values with water (not shown) as the bath medium 75. The dotted line represents the pre-defined threshold level. At several points on the curve in the solid line, lower fluorescence intensities are randomly recorded as compared to the dashed line. Also, the magnitudes of the drops in the intensities along the solid line is observed to be inconsistent. This does not result in any serious issue when both the solid line and the dashed line cross the dotted line at the same Ct value. However, as in the example shown in FIG. 1B, the solid line crosses the threshold level at Ct1 which is higher than the Ct value for the dashed line. Such inconsistency seriously affects diagnosis or detection of the target nucleic acid, thereby resulting in incorrect conclusions. Such a drift in the value of Ct is therefore likely to affect the extraction of the value of cycle threshold and the interpretation of the assay is thus likely to be unreliable.

The present invention provides an improved PCR apparatus which has higher accuracy of detection and analysis of the reaction material 21 when powder 76 is used as the bath medium 75 to exploit the benefits over liquid bath medium 75 as described above. This invention provides a great positive impact on biological analysis.

SUMMARY

Unless specified otherwise, the term "comprising" and "comprise" and grammatical variants thereof, are intended to represent "open" or "inclusive" language such that they include recited elements but also permit inclusion of additional, unrecited elements. The word "substantially" does not exclude completely. The terminologies 'first bath', 'second bath'... 'any bath' do not constitute the corresponding number of baths in a sequence but merely are names for ease of identification with respect to the purpose they serve. These baths may not represent separate physical entities as some of them may be sharable.

The inventor of this application diligently studied the issue of drift in the value of Ct as described in the previous section and arrived at the conclusion as described hereafter.

FIG. 1C is a sample photograph of fluorescent imaging using powder 76 as the bath medium 75 and at different stages of the thermal cycle with the same reactor 15. The images marked as 1 and 4 appear normal while the images marked as 2 and 3 have dark regions as shown by the arrows. FIG. 1D is another sample photograph of fluorescent imaging using powder 76 as the bath medium 75. The images marked as 2 and 3 appear normal while the image marked as 1 has an elongated dark region as shown by the arrow. All these images are obtained by conducting the imaging from the bottom of the reactors 15. The inventors attributed the reductions in the intensity levels in the solid line of FIG. 1B to such randomly occurring dark regions.

The inventors established that using powder 76 as the bath medium 75, some particles of powder 76 randomly remain adhered along the external surface of the reactor 15 when taken out of the baths 50 and 51. As illustrated in FIG. 2, the inventors attributed the dark spots in FIG. 1C to these particles of powder adhering to the surface of the reactor 15. The particles of the powder 76 block the incident illumination of the LED source from reaching the reaction material 21. Similarly, particles of the adhering powder 76 block the fluorescent rays from the reaction material 21 from reaching the detector. Thus, the fluorescence intensity for the detection reduces, thereby affecting the analysis. More the number of particles of the powder 76 adhering to the surface of the reactor 15, more are the number of dark spots generated and lower is the fluorescence intensity detected.

The inventors also established the fact that the number of particles of powder 76 adhering to the reactor 15 and thereby partially blocking the imaging is inconsistent during the process of thermal cycling and imaging. The elongated dark region in FIG. 1D is likely to be related to a cluster of particles of powder 76 adhering along a line or to a particle of the powder 76 that is of an elongated shape.

The inventors also established the fact that the chances of the particles adhering to the reactors 15 is higher for smaller particle sizes of the powder 76 and also depends on the materials of the powder 76 used such as metallic, ceramic, glass, plastics and the like. The materials of the reactor 15 like glass or plastic or ceramic and the like also have an effect on the adhesion.

As such, very minute quantities of the reaction materials 21 are processed in the reactors 15 to enable compactness of the apparatus 100 and efficient heat transfer during the thermal cycling. For the same reasons, the reactors 15 used are also of minimal sizes, with minimal wall thickness and diameter. No such issue of dark regions was detected if the LED illumination and imaging were conducted from the top of the reactor 15.

The particles of the powder 76 adhering to the body of the reactor 15 is a major issue that needs to be addressed.

According to a first aspect, an apparatus for thermal cycling for polymerase chain reaction (PCR) of nucleic acid is provided. The apparatus employs a reactor holder for holding reactor(s) to accommodate reaction material containing nucleic acid and the reactor(s) being in any form such as capillaries or tube(s) or well plate(s) or chip(s) or cartridge(s). The apparatus comprises:

a first bath; a second bath, in use bath media in the baths being respectively maintainable at two different temperatures;

a transfer means for allowing the reactor(s) to be in the two baths in a plurality of thermal cycles to alternately attain:

a predetermined high target temperature $T_{HT}$, and a predetermined low target temperature $T_{LT}$;

a florescent imaging means for imaging the reaction material during or after the thermal cycling; and the apparatus further comprises:

a powder-removing device such that in operation, before the imaging the powder-removing device mechanically removes particles of powder that adhere to the reactor(s), the powder being the bath medium in use in at least one of the baths.

Advantageously, the powder-removing device substantially removes the trace particles of powder that remain adhered along the body of the reactor(s) when taken out of the baths with powder as the bath medium. This significantly helps in achieving better quality and reliability of the fluorescence imaging for detection and analysis of the reaction material during the thermal cycling. Dropping the adhered particles onto a transparent window for the fluorescence imaging also undesirably blocks the imaging if conducted from the bottom side of the transparent window.

According to an embodiment, the powder-removing device is provided above the bath such that in operation the removed particles of powder drop into the bath. This also helps in retaining the volume of the powder bath medium in both the baths over the thermal cycles, thereby practically requiring no refill. In addition, dropping the particles of powder in the corresponding bath lessens the effect of offsetting the temperature in either bath during the thermal cycling and particularly for a batch process with a large array of reactors. Using powder as the bath medium facilitates the concept of temperature offset to enhance the speed of the PCR as taught by the patent application no: PCT/SG2017/050293, where the bath temperature of the first bath is maintained well above the predetermined high target temperature $T_{HT}$, and the bath temperature of the second bath is maintained well below the predetermined low target temperature. Higher the difference between the bath temperature and the target temperature, the effect of offsetting gets higher. By dropping the particles of the powder into the corresponding bath, this temperature offset is better maintained. Additionally, since powder as the bath medium provides no heat transfer due to convection like with a liquid as the bath medium, the powder towards the surface of the bath undergoes more exchange of heat with the ambience. As a result, the reaction material along the depth of the reactor(s) particularly when in the form of capillary tube may undesirably be subjected to a temperature gradient. Having the powder-removing device above the baths help to reduce the temperature gradient between the top and bottom regions of the baths. In addition, this embodiment prevents dropping of the particles of powder outside the baths but within the apparatus during the movement of the reactor(s) by the transfer means for thermal cycling, fluorescence imaging and the kind. Dropping of the particles of the powder within the apparatus can be harmful to the mechanical and electrical systems in terms of causing mechanical jams and electrical short circuits respectively.

According to yet another embodiment, the removed particles of powder drop into a container. This feature is advantageous when the powder adhering to the reactor(s) withdrawn from any of the baths is removed at a common place and dropped into a common container. This requires lesser complexity of the apparatus as compared to the embodiment where the powder removing device needs to remove the adhered powder at each of the baths containing powder as the bath medium.

According to an embodiment, operationally the powder-removing device executes movement(s) by electromechanical means. This feature enables a more efficient removal of the trace particles of powder, though is at the cost of foot-print and complexity of the apparatus. The movement may be of any kind such as rotational or translational.

According to an embodiment, the powder-removing device comprises an elastic surface for contacting the reactor(s). The elastic or elastic surface allows a tighter fit between the reactor(s) and the powder-removing device for a more effective removal of the particles of powder. The tight fit however needs to be optimized so as not to affect the speed of the PCR. According to yet another embodiment, the powder-removing device comprises a surface with bristles for contacting the reactor(s). The higher flexibility in the shape of the bristles help in an effective removal of the particles of powder. The bristles may have a plurality of lengths so that when the reactor(s) is/are moved over the bristles, both the side as well as the bottom of the reactor(s) are cleaned to remove the adhered powder.

According to an embodiment, the powder-removing device comprises a fabric coated surface, the fabric being for contacting the reactor(s). The fabric allows a tight fit between the reactor(s) and the powder-removing device.

According to an embodiment, the powder-removing device comprises an air jet that contacts the reactor(s) for removing the adhered powder particles. Advantageously the air jet continuously provides a fresh cleaning surface. The direction of the jet however needs to be such that the particles of powder fall into the baths or into the container and not spread over other areas of the apparatus. In operation, the air jet may be maintainable at a third predetermined temperature to maintain the reactor(s) at a desired temperature particularly during the fluorescence imaging being conducted during annealing or extension. Guarding means may also be provided to assist the removed particles of powder to fall into the baths or into the container.

According to an embodiment, the powder-removing device comprises a first layer and a second layer in a stack, such that in operation the reactor(s) passes/pass through both. According to an embodiment, the first layer and the second layer are in mutually orthogonal directions. This provides a more complete removal of the particles all around the reactor surface.

According to an embodiment, the first layer comprises a plurality of first elastic flaps and the second layer comprises a plurality of second elastic flaps, and the first and second elastic flaps are mutually misaligned along an axis vertical to the first layer and the second layer. This enables a more efficient removal of the particles all around the reactor surface.

According to an embodiment, the first layer comprises first elastic bristles and the second layer comprises second elastic bristles, and the first and second elastic bristles are mutually misaligned along an axis vertical to the first layer and the second layer. This enables a more efficient removal of the particles all around the reactor surface.

According to an embodiment, the powder-removing device comprises a high temperature resistant surface for contacting the reactor(s) when in operation, the surface being able to tolerate temperatures above 100 degrees Celsius. This feature is useful when the bath temperatures are to be maintained at temperatures higher than the target temperatures in order to speed up the process of thermal cycling with temperature-offset as taught in the patent application PCT/SG2017/050293. The reactor(s) is/are taken out of the bath upon attaining the target temperature. However, while the trace particles of the powder adhering to the reactor body are removed with the powder-removing device, the powder is likely to remain closer to the bath temperature.

According to an embodiment, in use the powder-removing device is located on a top open side of the at least one of the baths such that the device substantially covers the open side, and enables the reactor(s) to be inserted through the device into the bath medium and taken out. This feature helps to reduce heat loss to the ambient from the heated baths, from the top open side. This helps to maintain the temperatures of the bath medium more uniform along the vertical direction. Thus, the reactor(s) is/are subjected to a more uniform temperature gradient along their vertical lengths allowing a more reliable PCR.

According to an embodiment, in use the powder-removing device covers the open side securely enough to prevent the powder from spilling out when the bath is not held upright, the powder having a largest dimension of 5 millimeters. This feature is useful particularly during shipment, transportation, or any other change of location for the apparatus where it is likely to suffer some tilts.

According to an embodiment, the powder-removing device comprises a plurality of portions that in operation contact the reactor(s) by clamping at least a portion of the reactor(s), for removal of the powder. Advantageously, in operation the device may be made to come in contact with the reactor(s) only during lifting out of the bath and not during insertion into the bath. If the device is located outside the bath areas for removal of the powder before fluorescence, the reactor(s) may pass through the device only once. This reduces wear and tear of the portions of the device that come in contact with the reactor(s). According to an embodiment, the tightness of the clamping is adjustable to suit the material of the powder and the particle size of the powder.

It also helps to adjust the tightness of the clamping that mechanically changes with time and use of the device.

BRIEF DESCRIPTION OF THE DRAWINGS

In the following drawings, same reference numbers generally refer to the same parts throughout. The drawings are not to scale, instead the emphasis is on describing the concept.

FIG. 1A is a schematic view of a typical set up in the art for thermal cycling of a reaction material containing nucleic acid, where powder is used as the bath medium.

FIG. 1B is a sample PCR Ct plot with the set up as at FIG. 1A, using powder and water as the bath media.

FIG. 2 is a schematic view of a theory developed to explain the observations as described at FIGS. 1B-1D.

FIG. 4A shows a cross-sectional view of an embodiment of the invention where the powder-removing device comprises bristles fixed around a rod.

FIG. 4B shows a cross-sectional view of an embodiment of the invention where the powder-removing device comprises a fabric fixed around a rod.

FIG. 4C shows a cross-sectional view of an embodiment of the invention where the powder-removing device comprises a fabric fixed around a rod with a gap in between.

FIG. 5A is an elevational and cross-sectional view of an embodiment of the invention where the reactor with particles of the powder adhered is being passed through the powder-removing device.

FIG. 5B is a view of FIG. 5A after the reactor is passed through the powder-removing device and the adhered particles of the powder are removed.

FIG. 6A is an elevational and cross-sectional view of an embodiment of the invention for the powder-removing device that is located outside the baths.

DETAILED DESCRIPTION OF THE EMBODIMENTS

The following description presents several preferred embodiments of the present invention in sufficient detail such that those skilled in the art can make and use the invention.

The structure and configuration of the baths disclosed under this invention do not limit the scope of achieving any kind of thermal profile. Any user specified thermal profile may be attained by suitably placing the reactors in a specified sequence and for specified time periods in the baths that are maintained at pre-determined temperatures. More than two baths may be employed to achieve any user specified thermal profile.

Figure 1C:
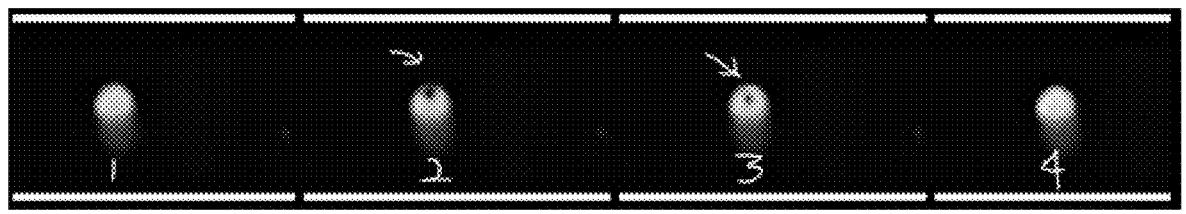
FIG. 1C is a view of four fluorescence images at different stages of thermal cycling using the set up as at FIG. 1A with powder as the bath medium.
Figure 3A:
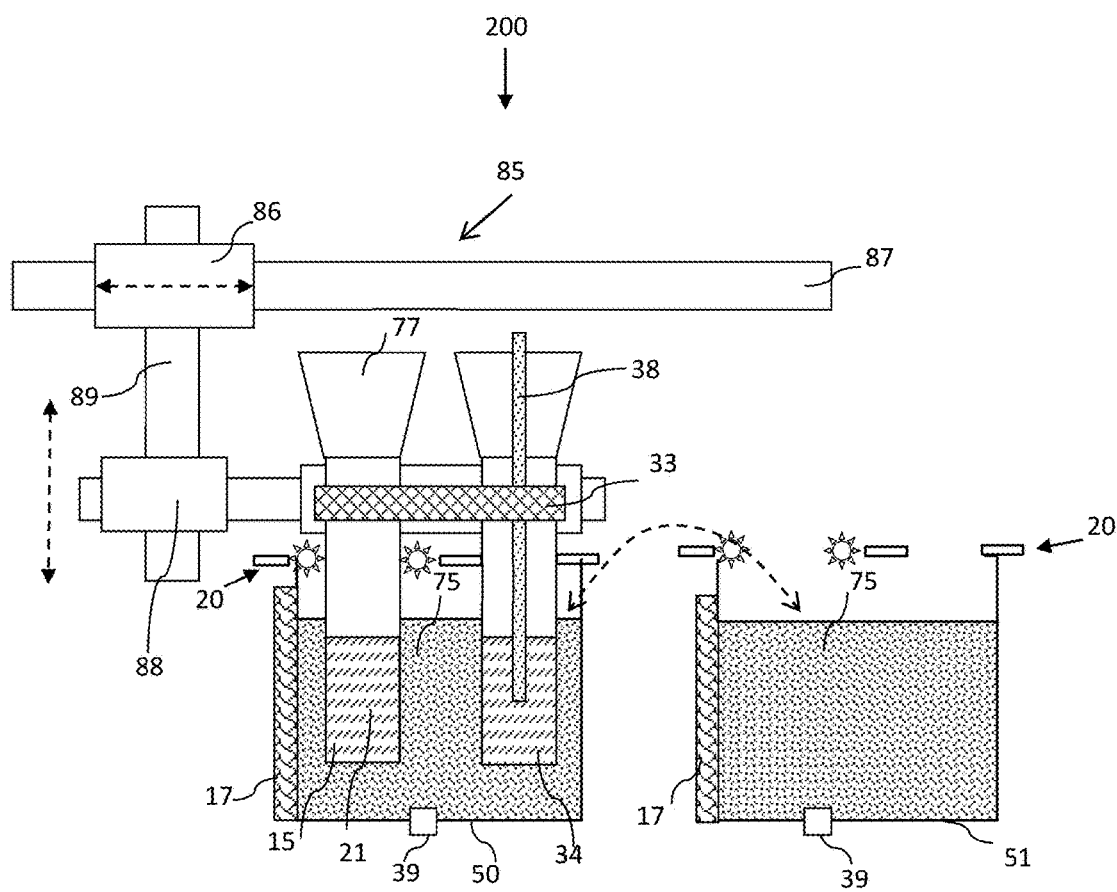
FIG. 3A is a schematic view of FIG. 1A incorporating the powder-removing device according to an embodiment of the invention.

FIG. 3A illustrates an embodiment of the apparatus 200 with reference to the set-up for FIG. 1A with the powder-removing device 20 for both the baths 50, 51. Herein, the powder-removing device 20 is provided above the bath medium 75. The reactor 15 passes through the powder-removing device 20 after coming out of the baths medium 75. Upon removal by the powder-removing device 20, advantageously the adhering particles of powder 76 drop back into the corresponding baths 50, 51. By virtue of the design, the reactor 15 passes through the powder-removing device 20 while entering the baths medium 75 as well though this is not a required feature. Special mechanism may be provided to move away the powder-removing device 20 at this stage at the cost of complexity. The main objective is to remove the particles of powder 76 before the fluorescence imaging at any stage during or after the thermal cycling.

Figure 3B:
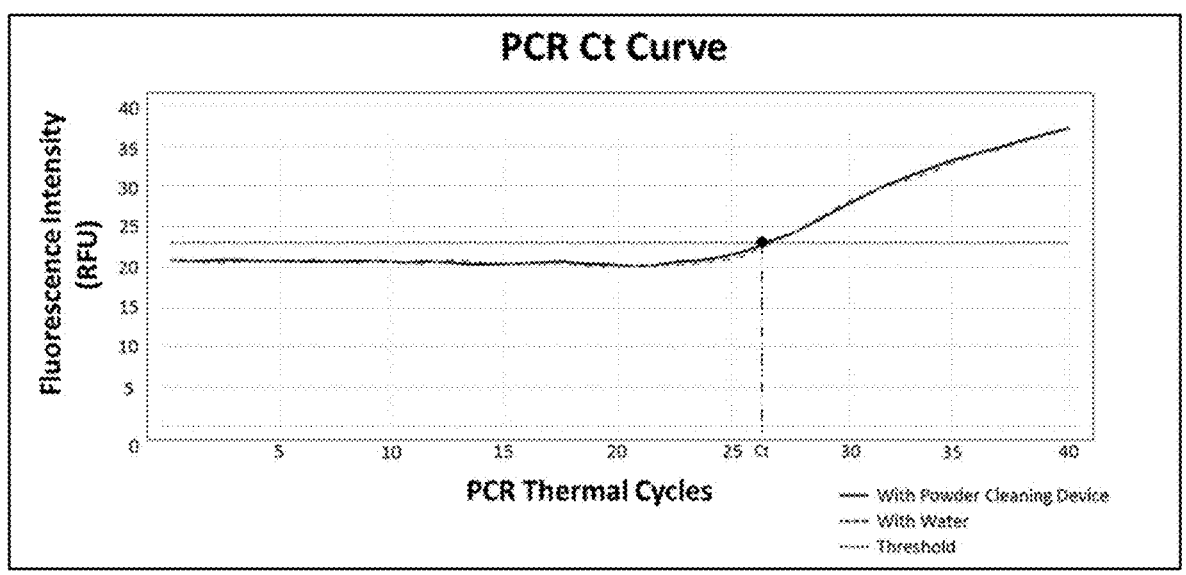
FIG. 3B includes sample PCR Ct plots with the set up as at FIG. 3A, using the powder-removing device with powder as the bath medium.

FIG. 3B includes sample PCR Ct plots with the set up as at FIG. 3A, using the powder-removing device 20 with powder 76 as the bath medium 75. It may be noted that with the use of the powder-removing device 20, lower fluorescence intensities like those detected in FIG. 1B on the curve in the solid line have advantageously been eliminated. Similar result has been observed with a large number of reactors 15 undergoing thermal cycling with the powder bath medium 75 and passing through the powder-removing device 20 before imaging. This substantiates the proposed theory under FIG. 2.

The powder removing device 20 may be in any form. The cross-sectional view at FIG. 4A shows bristles 22 around a rod 24 included in the powder-removing device 20 according to an embodiment of the invention. The cross-sectional view at FIG. 4B shows a fabric 23 fixed around a rod 24 included in the powder-removing device 20 according to an embodiment of the invention. FIG. 4C shows a cross-sectional view of an embodiment of the invention where the powder-removing device 20 comprises a fabric 23 fixed around a rod 24 with a gap in between to provide more flex of the fabric 23 to accommodate the passage of the reactor 15.

FIG. 5A in an embodiment of the invention illustrates the reactor 15 with particles of the powder 76 adhered being passed through the powder-removing device 20.

FIG. 5B is a view of FIG. 5A after the reactor 15 is passed through the powder-removing device 20 and the adhered particles of the powder 76 are removed. It may be appreciated that the gaps on either side between the reactor 15 and the powder-removing device 20 need to be smaller than the smallest dimension of the particles of the powder 76.

Figure 1D:
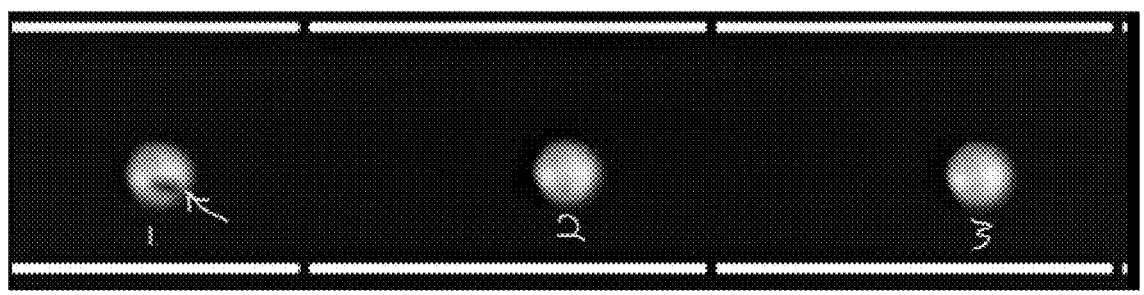
FIG. 1D is a view of three fluorescence images at different stages of thermal cycling using the set up as at FIG. 1A with powder as the bath medium.

FIG. 6A is an embodiment of the invention for the powder-removing device 20 that is located outside the baths 50, 51. Herein, the reactor 15 passes through the powder-removing device 20 outside the baths 50/51 and before the step of imaging. In this embodiment, an empty tank 81 has been shown which is transparent to the imaging light spectrum. The empty tank 81 collects the particles of powder 76 that drop after passing through the powder-removing device 20. This embodiment is suitable for conducting imaging from the side of the reactor 15 as shown. Imaging conducted from the bottom is likely to cause the same issues as described under FIGS. 1B, 1C, and 1D. The empty tank 81 may be maintained at a specified temperature as suitable for conducting the imaging.

Figure 6B:
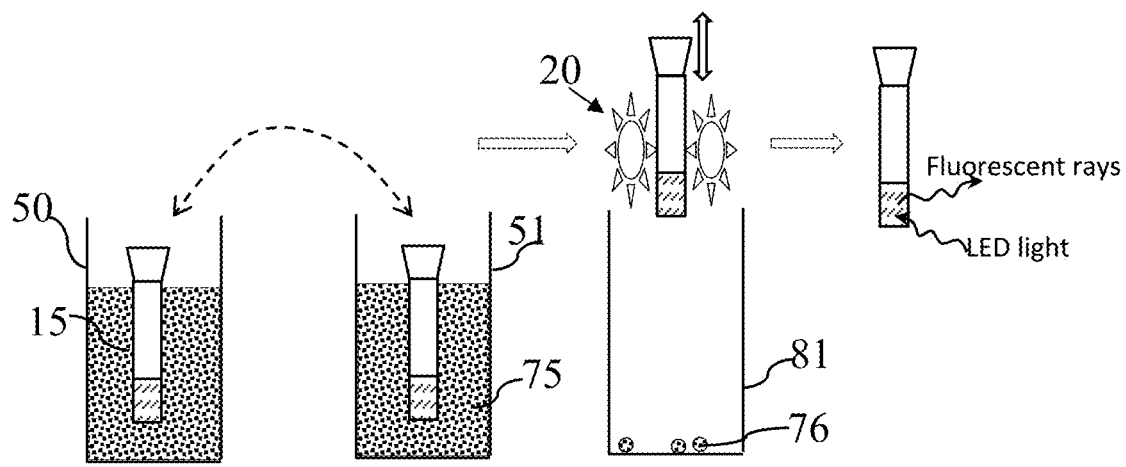
FIG. 6B is an elevational and cross-sectional view of an embodiment of the invention for the powder-removing device that is located outside the baths.

FIG. 6B shows another embodiment of the invention for the powder-removing device 20. Herein, the reactor 15 passes through the powder-removing device 20 before the step of imaging. In this embodiment, an empty tank 81 has been shown for collecting the particles of powder 76 and the imaging is done at a different location. In this embodiment, the issue of dropped-off particles of powder 76 has been addressed for imaging conducted from the bottom. Thus, in this embodiment the imaging can be conducted from the side or from below the reactor 15, as desired.

Figure 6C:
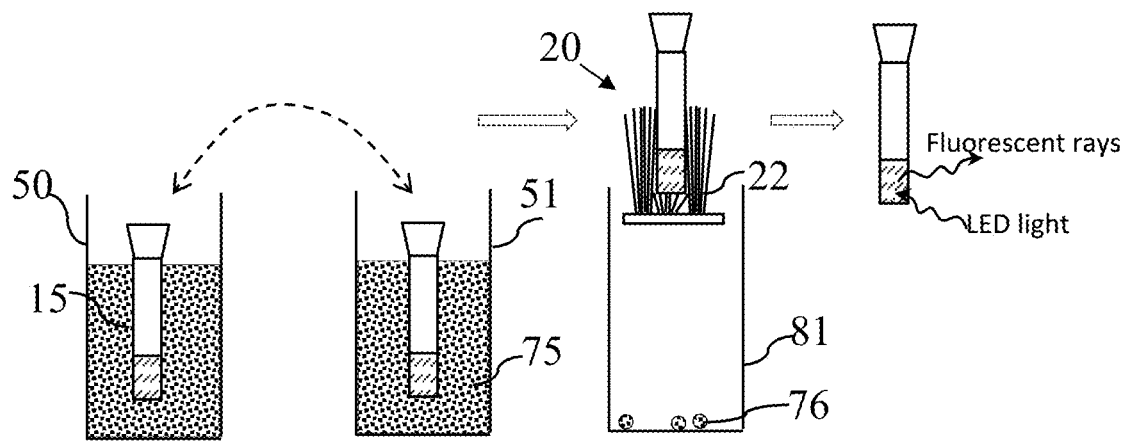
FIG. 6C is an elevational and cross-sectional view of an embodiment of the invention for the powder-removing device that is located outside the baths.

FIG. 6C shows yet another embodiment of the invention for the powder-removing device 20. Herein the powder-removing device 20 comprises bristles 22 in the vertical direction. The bristles 22 are of shorter and longer sizes so that when the reactor 15 passes through horizontally, the longer sized bristles 22 help to remove the particles of powder 76 adhering on the side of the reactor 15 and the shorter bristles 22 help to remove the particles of powder 76 adhering on the bottom of the reactor 15. The removed particles of the powder 76 are collected in an empty tank 81. The reactor 15 then proceeds for fluorescence imaging outside the tank 81.

Figure 7A:
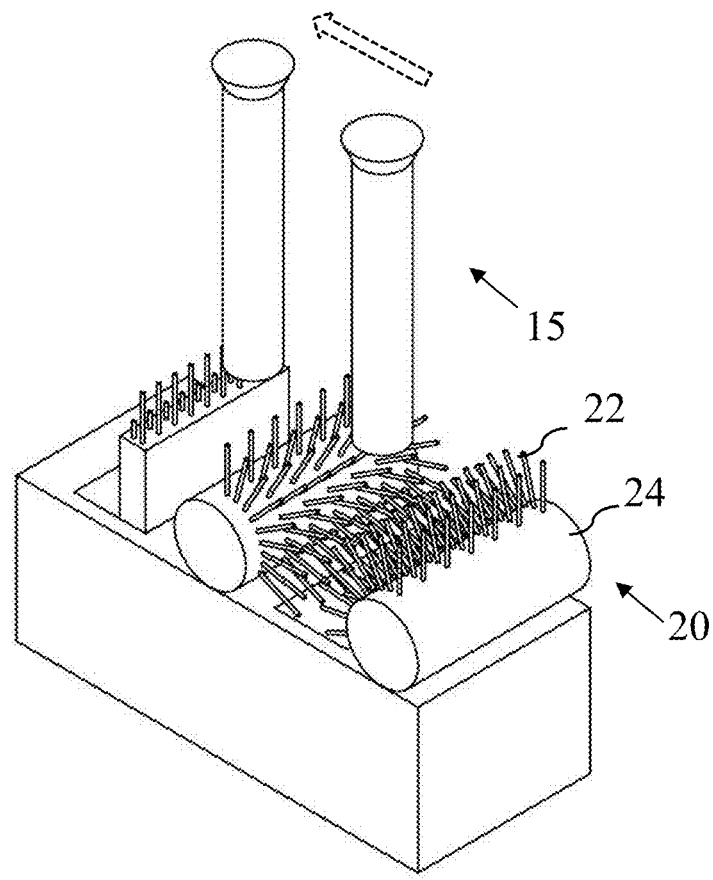
FIG. 7A is a perspective view of an embodiment of the invention for the powder-removing device.

FIG. 7A is a perspective view of an embodiment of the invention for the powder-removing device 20. As illustrated by the dashed and block arrow, herein the reactor 20 horizontally moves over the bristles 22 radially arranged over two rods 24 and then over vertical bristles 22. The radial bristles 22 are effective in removing the particles of powder 76 adhering to the reactor 15 along the side and the vertical bristles 22 are effective in removing the particles of powder 76 adhering to the reactor 15 along the bottom. Combination of various sizes of the bristles 22 may be used for a more effective removal of the particles of powder 76.

Figure 7B:
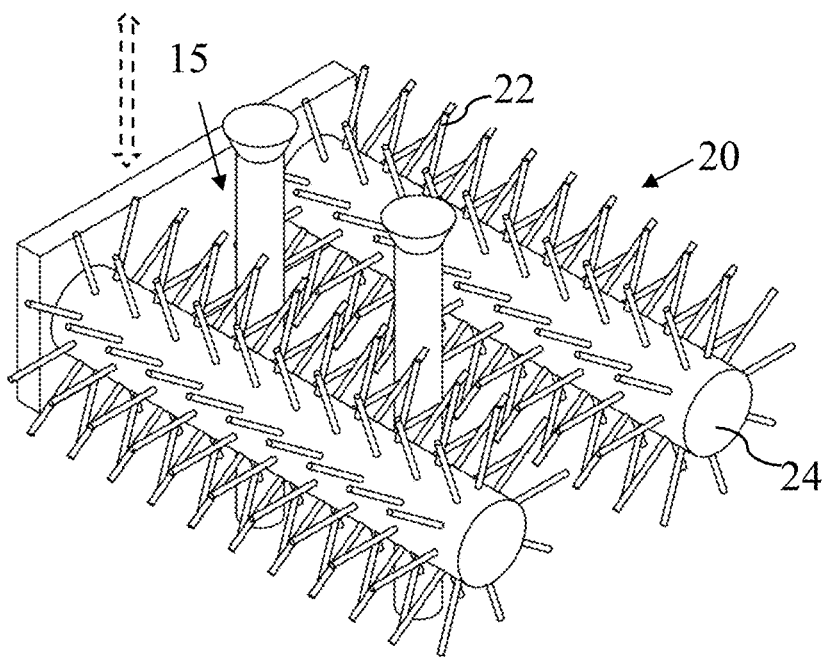
FIG. 7B is a perspective view of an embodiment of the invention for the powder-removing device.

FIG. 7B is a perspective view of an embodiment of the invention for the powder-removing device 20. As illustrated by the dashed and block arrow, herein the reactor 20 vertically moves through the bristles 22 radially arranged over two rods 24. The radial bristles 22 are effective in removing the particles of powder 76 adhering to the reactor 15 along the side for fluorescence imaging to be conducted from the side of the reactor 15. Combination of various sizes of the bristles 22 may be used for a more effective removal of the particles of powder 76.

Figure 7C:
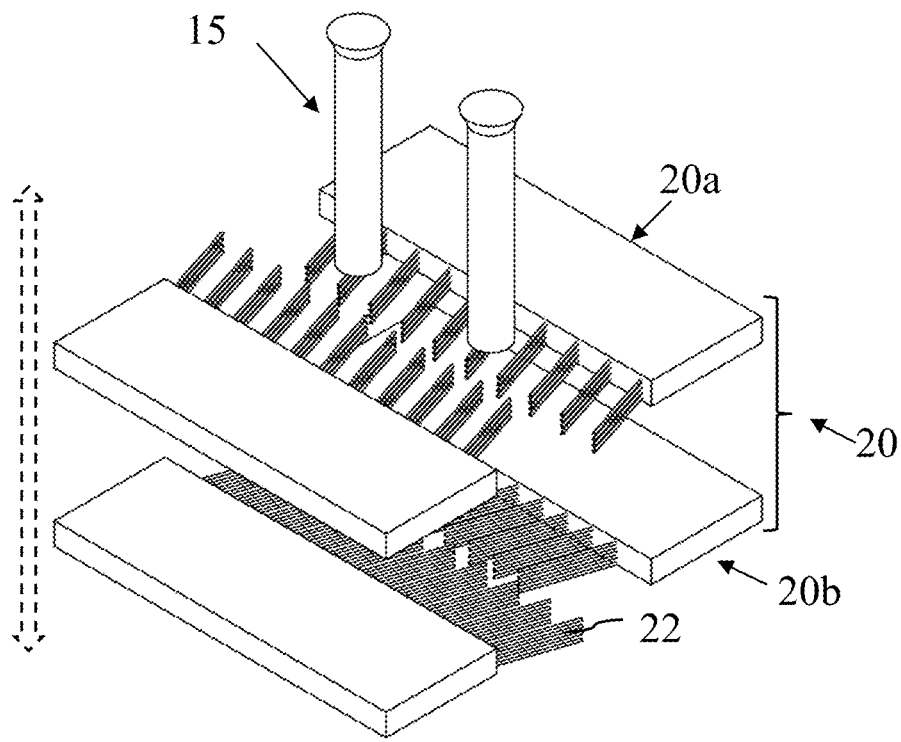
FIG. 7C is a perspective view of an embodiment of the invention with a double layered powder-removing device.

FIG. 7C is a perspective view of an embodiment of the invention for the powder-removing device 20. As illustrated by the dashed and block arrow, herein the reactor 20 vertically moves through the bristles 22 parallelly arranged. The powder-removing device 20 has a stack of a first layer 20a and a second layer 20b with the bristles 22 in the layers being arranged at an angle with each other. In operation, the powder-removing device 20 contacts the reactor 15 via the two layers 20a, 20b as shown. The parallel bristles 22 are effective in removing the particles of powder 76 adhering to the reactor 15 along the side for fluorescence imaging to be conducted from the side of the reactor 15. Combination of various sizes of the bristles 22 may be used for a more effective removal of the particles of powder 76.

Figure 8A:
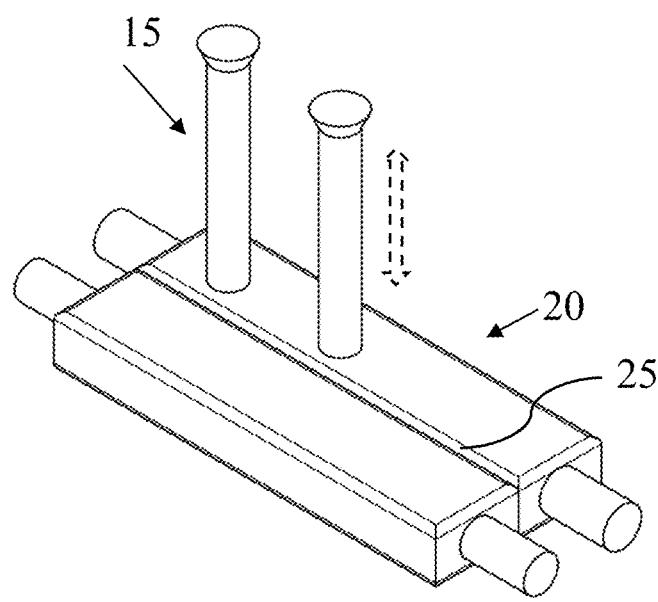
FIG. 8A is a perspective view of an embodiment of the invention with the powder-removing device comprising elastic edges.
Figure 8B:
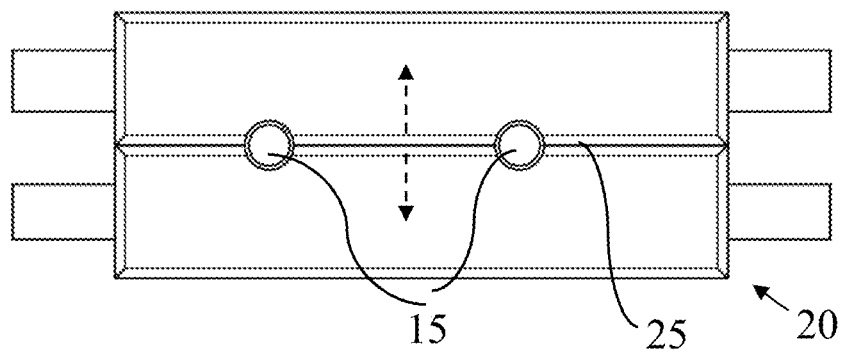
FIG. 8B is a plan view of FIG. 8A.
Figure 8C:
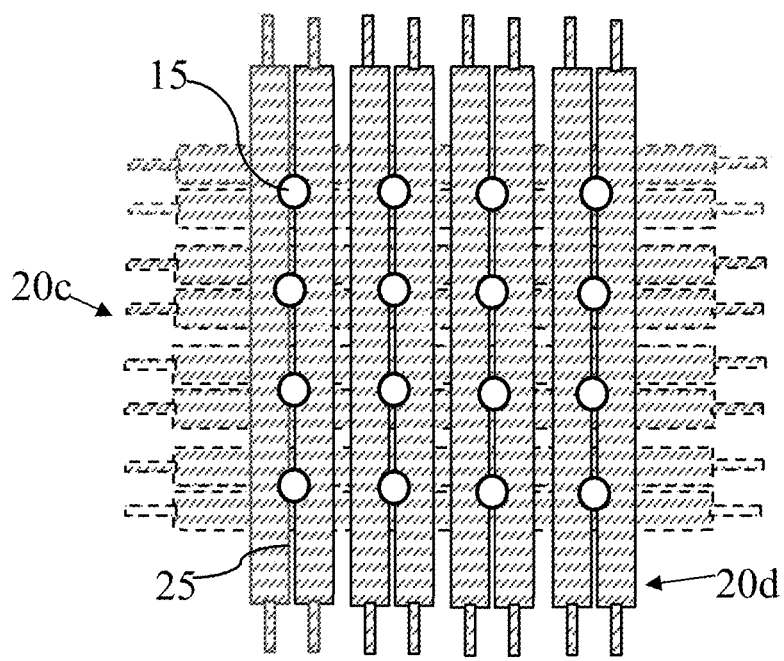
FIG. 8C is a part plan view of a first and a second layer, each comprising multiple pieces of the device as similar to FIG. 8B with the elastic edges of the two layers being orthogonally oriented to each other, with a matrix of the reactors passing through both.
Figure 8D:
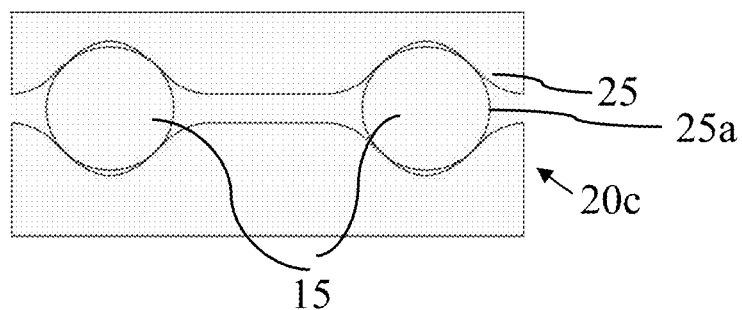
FIG. 8D is a part view of FIG. 8C where the reactors are inserted through the elastic edges of one of the devices in the first layer shown along the horizontal direction.
Figure 8E:
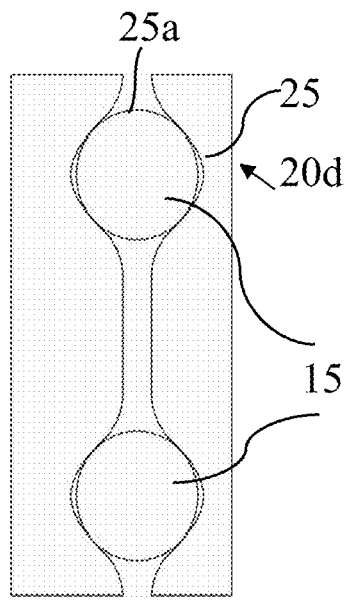
FIG. 8E is a part view of FIG. 8C where the reactors are inserted through the elastic edges of one of the devices in the second layer shown along the vertical direction.

FIG. 8A is a perspective view of an embodiment of the invention with the powder-removing device 20 comprising closely spaced elastic edges 25. As illustrated by the dashed and block arrow, herein the reactor 15 vertically moves through the elastic edges 25. In operation, the elastic edges 25 contact the reactor 15 and help in removing the particles of powder 76 adhering to the reactor 15 along the side for fluorescence imaging to be conducted from the side of the reactor 15. FIG. 8B is a plan view of FIG. 8A. The dashed arrows illustrate that the elastic edges 25 move in opposite directions to accommodate the passage of the reactor 15. FIG. 8C is a part plan view of a double layered power-removing device 20 having a first layer 20c shown in dashed lines and a second layer 20d as shown in solid lines, each comprising multiple pieces of the device 20 as similar to FIG. 8B with the elastic edges 25 of the two layers 20c and 20d being orthogonally oriented to each other, with a matrix of the reactors 15 passing through both. FIG. 8D is a part view of FIG. 8C where two reactors 15 are inserted through the elastic edges 25 of one of the devices 20 in the first layer 20c shown along the horizontal direction. In reality, upon the insertion the elastic edges 25 may not be exactly conformal all around the reactors 15 thereby generating some gaps 25a as shown. Such a scenario may be inefficient in a removal of the particles of powder 76 all around the reactor 15. FIG. 8E shows the second layer 20c of the elastic edges 25a that is orthogonal to the first layer 20d. This helps to remove the particles of powder 76 that are not removed by the first layer 20c.

According to an embodiment, as shown by the dashed arrows in FIG. 8B, in operation the elastic edges 25 move in opposite directions to accommodate the passage of the reactor 15 to generate sufficient gaps so that the device 20 does not make contact with the reactors 15 when being inserted into the baths 50, 51. When the reactors 15 are taken out of the bath 50, 51 the elastic edges 25 come closer to clamp the reactors 15.

Figure 9A:
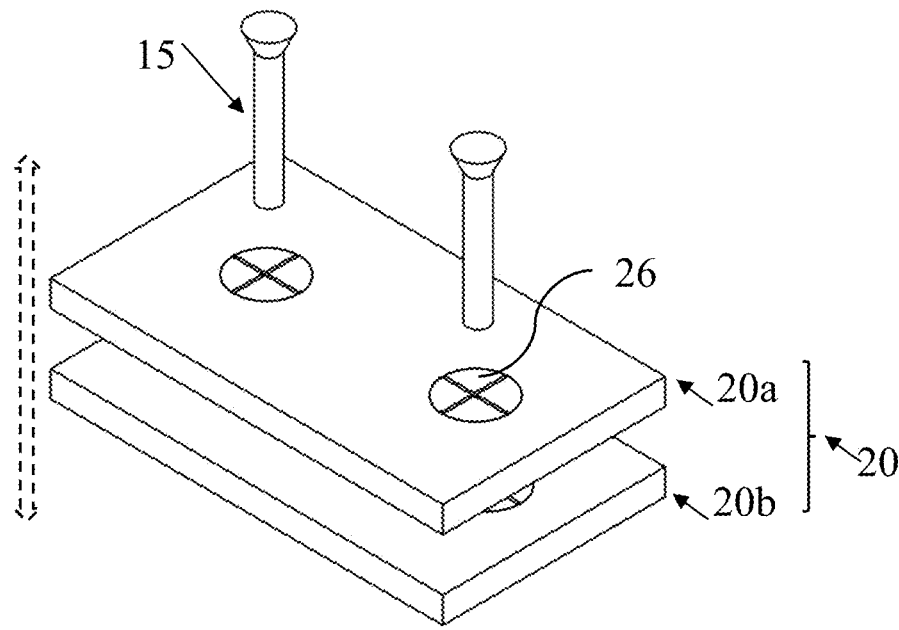
FIG. 9A is a perspective view of an embodiment of the invention with a double layered powder-removing device having elastic flaps.
Figure 9B:
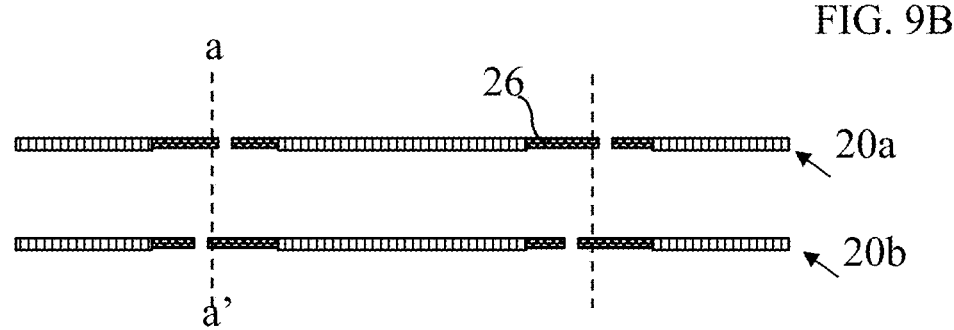
FIG. 9B is an elevational cross-sectional view of FIG. 9A where the elastic flaps in the two layers are axially off-centered.

FIG. 9A is a perspective view of an embodiment of the invention showing a stacked double layered powder-removing device 20 having elastic flaps 26 formed by four sectors. The dashed block arrow shows the direction of movement of the reactors 15 through the elastic flaps 26. FIG. 9B illustrates how the elastic flaps 26 in the two layers 20a and 20b are off-centered from an axis a-a' that is vertical to the two layers 20a and 20b and such off-centering being in mutually opposite directions with reference to the axis a-a', for a more efficient removal of the particles of the powder 76. This also compensates for minor misalignments occurring in the position of the reactor 15 relative to the powder-removing device 20 due to fatigue of the reactor transfer mechanism 85 over time.

Figure 10A:
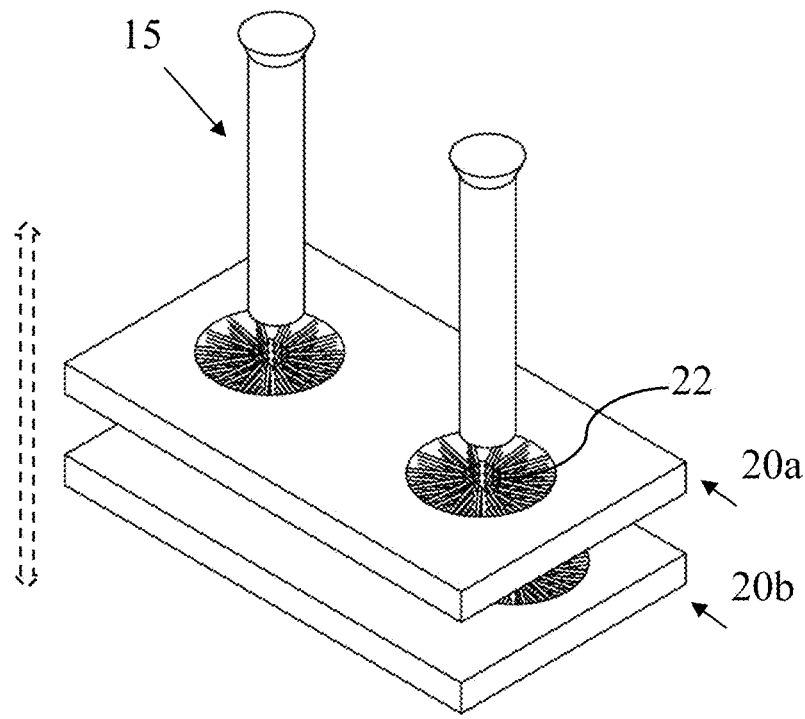
FIG. 10A is a perspective view of an embodiment of the invention with a double layered powder-removing device having bristles.
Figure 10B:
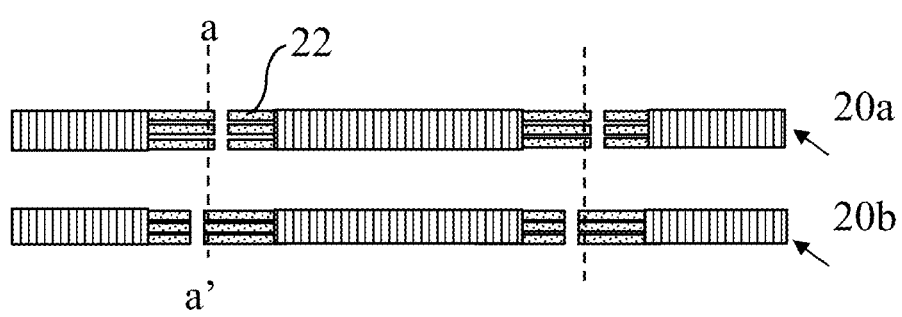
FIG. 10B is an elevational cross-sectional view of FIG. 9A where the bristles in the two layers are axially off-centered.

FIG. 10A is a perspective view of an embodiment of the invention with a stacked double layered powder-removing device 20 having bristles 22. FIG. 10B illustrates how the bristles 22 in the two layers 20a and 20b are off-centered from an axis a-a' that is vertical to the two layers 20a and 20b and such off-centering being in mutually opposite directions with reference to the axis a-a', for a more efficient removal of the particles of the powder 76. This also compensates for minor misalignments occurring in the position of the reactor 15 relative to the powder-removing device 20 due to fatigue of the reactor transfer mechanism 85 over time.

Figure 11A:
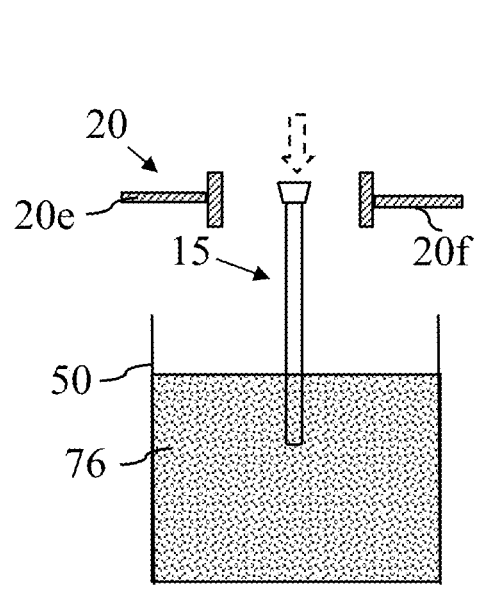
FIG. 11A is an elevational cross-sectional view of an embodiment of the invention where the powder-removing device has two portions that do not contact the reactor while being inserted into the powder bath medium.
Figure 11B:
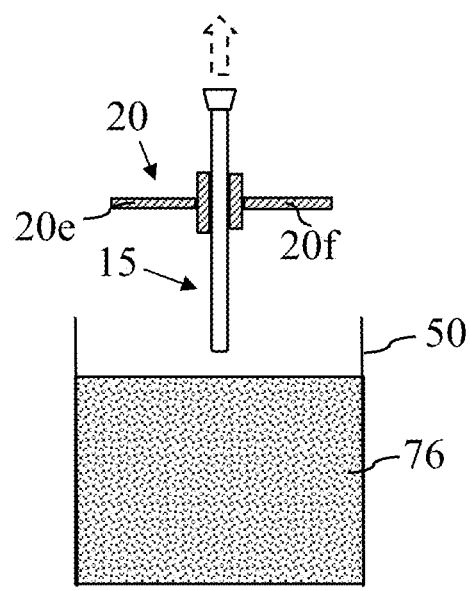
FIG. 11B is an elevational cross-sectional view of the embodiment of the invention at FIG. 11A where the two portions contact the reactor while being lifted out of the powder bath medium.

FIG. 11A is an elevational cross-sectional view of an embodiment of the invention where the powder-removing device 20 has two portions 20e, 20f that do not contact the reactor 15 while being inserted into the powder 76 that is being used as the bath medium 75 in the bath 50. According to other embodiments, more than two portions 20e, 20f may be used. FIG. 11B is an elevational cross-sectional view of the embodiment of the invention at FIG. 11A where the two portions 20e and 20f contact the reactor 15 while being lifted out of the powder 76, so that the particles of the powder 76 adhering to the body of the reactor 15 are removed. In this embodiment the particles of the powder 76 fall back into the bath 50. The portions 20e, 20f may clamp the reactor 15 all around the outer surface so that substantially all the particles of powder 76 are removed while lifting out of the bath 50. The same mechanism may be provided for the other baths in the apparatus 200 as well. Advantageously, in operation the device 20 is allowed to come in contact with the reactor 15 only during lifting out of the bath 50 or 51 and not during insertion into the bath 50 or 51. Similarly, if the device 20 is located outside the bath 50, 51 areas for removal of the powder 76 before fluorescence, the reactor 15 passes through the device 20 only once. This reduces wear and tear of the portions of the device 20 that come in contact with the reactor 15. The tightness of the clamping the reactor 15 may be adjustable to suit the material of the powder 76 and the particle size of the powder 76. It also helps to adjust the tightness of the clamping that mechanically changes with time and use of the device 20. Though only one reactor 15 has been shown here, the same concept may be used for multiple reactors 15 as well.

According to an embodiment, in use the powder-removing device 20 is located on a top open side 49 of the at least one of the baths 50, 51 such that the device 20 substantially covers the open side 49, while enabling the reactor(s) 15 to be inserted through the device 20 into the bath medium 75 and taken out. Optionally, the powder-removing device 20 may cover the open side 49 securely enough to prevent the powder 76 from spilling out when the bath 50, 51 are not held upright, the powder 76 having a largest dimension of 5 millimeters.

It will be appreciated by those skilled in the art that the flexibility of the bristles 22, the fabric 23, the elastic edges 25 and the elastic flaps 26 need to be such that the speed of the PCR is not affected. The bristles 22 may be made of any suitable material like metal, fabric, animal hair, synthetic fibers, and the kind.

The powder 76 may be of any type, such as ceramic, metallic like copper, glass, plastic, and the kind. Any of these may be dispersed in a liquid as well. The powder may preferably have a thermal conductivity that is more than 0.3 watts per meter-kelvin (W/m·K).

No retardation in the speed of PCR has been observed due to the introduction of the powder-removing device 20. Guards (not shown) may be provided to confine the removed powder 76 to within a specified region. Smaller particles sizes for the powder 76 is favorable to protect the reactors 15 from breakage particularly when in the form of capillaries. Besides, smaller particle sizes provide more efficient exchange of heat with the reactors 15 due to increased compactness and lesser voids. However, smaller the size of the particles of powder 76, more is the adhesion with the reactor 15 hence more is the requirement of the powder-removing device 20. The extent of the adhesion is also dependent on factors like the combinations of the materials of the powder 76 and reactors 15 used like metallic, ceramic, glass, plastics, and the kind.

Though more reaction material 21 is better for analysis, reactors 15 in the form of capillaries are preferred for fast PCR. The length of the commercially available capillaries is typically 10-20 mm. The areas of the baths 50, 51 need to be big enough to allow easier movement of the powder 76 in order to prevent the delicate capillaries from breakage. The gradient of the temperature along the depth of the powder 76 is lesser with reduced particle sizes.

According to other embodiments, more baths may be used as required. The reactor 15 may be in any form, such as capillaries, tube(s), well plate(s), chip(s) or cartridge(s). A third bath (not shown) may be used for the reactor 15 to attain a predetermined medium target temperature, corresponding to the extension of primers in nucleic acid or the annealing of primers or probes onto nucleic acid.

The reactors 15 may be made up of any suitable material such as plastics, elastomer, glass, metal, ceramic, and their combinations, in which the plastics include polypropylene and polycarbonate. The glass reactor 15 can be made in a form of a glass capillary of small diameters such as 0.1 mm-3 mm OD and 0.02 mm-2 mm ID, and the metal can be aluminum in form of thin film, thin cavity, and capillary. Reaction materials 21 can be made from non-biological active substances with chemical or biological stability. At least a portion of the reactor 15 is preferred to be transparent. In another embodiment, the reactors 15 can be in a form of a reactor array chip or a microfluidic reactor chip or arrayed chip. For example, the reactors 15 can be in a form of wells or channels of a substrate plate and optionally covered with a solid layer of material to form closed reaction chambers, in which the reaction fluid or reaction system is situated. The reaction material 21 in all the reactors 15 in the reactor holder 33 may not be identical. Simultaneous PCR can be advantageously conducted for different materials 21 if the bath temperatures are suitable. At least a part of the reactor wall is made of transparent material in order to enable the imaging and detection process. When using the above described apparatus 100 or 200 for nucleic acid analysis and processing, the reaction material 21 comprises reaction constituents including at least one enzyme, nucleic acid and/or particle containing at least one nucleic acid, primers for PCR, primers for isothermal amplifications, primers for other nucleic acid amplifications and processing, dNTP, $Mg^{2+}$, fluorescent dyes and probes, control DNA, control RNA, control cells, control micro-organisms, and other reagents required for nucleic acid amplification, processing, and analysis. The particle containing nucleic acid mentioned above comprises at least one cell virus, white blood cell and stromal cell, circulating tumor cell, embryo cell. One application may be to use the apparatus 100 to test different kinds of reaction materials 21 against the same set of primer and probes, such as test more than one sample. For such application, different kinds of reaction material 21 containing no target primers and/or probes are each loaded into one reactor 15 in a reactor-strip 4, with all the reactors 15 being pre-loaded with the same set or the same sets of PCR primers and/or probes. For the same application, different kinds of reaction materials 21 pre-mixed with respective PCR target primers and/or probes are each loaded into one reactor 15 in a reactor-strip 4, with all the reactors 15 being not pre-loaded with the same set of PCR primers and or probes. The reaction materials 21 can include control genes and/or cells and corresponding fluorescent dyes or probes. In the above situations, the different probes emit light of different wavelengths. Another application of the methods and devices are used to test the same reaction material 21 against different sets of primer and probes. One example of such an application is to test one type of sample for more than one purpose. For this application, a single reaction material 21 is added into the reactors 15 each loaded with at least one different set PCR primers and or probes. The reaction material 21 can include control genes and/or cells and corresponding fluorescent dyes or probes. In the above situations, the different probes emit light of different wavelengths. The above reaction material 21 is used in polymerase chain reaction, reverse transcription-PCR, end-point PCR, ligase chain reaction, pre-amplification or target enrichment of nucleic acid sequencing or variations of polymerase chain reaction (PCR), isothermal amplification, linear amplification, library preparations for sequencing, bridge amplification used in sequencing. The variation of the polymerase chain reaction mentioned above comprises reverse transcription-PCR, real-time fluorescent quantitative polymerase chain amplification reaction and real-time fluorescent quantitative reverse transcription polymerase chain amplification reaction, inverse polymerase chain amplification reaction, anchored polymerase chain amplification reaction, asymmetric polymerase chain amplification reaction, multiplex PCR, colour complementation polymerase chain amplification reaction, immune polymerase chain amplification reaction, nested polymerase chain amplification reaction, the target enrichment of pre-amplification or nucleic acid sequencing, ELISA-PCR.

From the foregoing description, it will be understood by those skilled in the art that many variations or modifications in details of design, construction and operation may be made without departing from the present invention as defined in the claims.

What is claimed is:

1. An apparatus for thermal cycling for a polymerase chain reaction (PCR) of nucleic acid, wherein the apparatus employs a reactor holder for holding at least one reactor to accommodate a reaction material containing the nucleic acid, and the at least one reactor is reactor in a form selected from the group consisting of capillaries, tubes, wellplates, chips, and cartridges, and the apparatus comprises:

two baths comprising a first bath and a second bath, wherein in use, bath media comprising a bath medium in the first bath and a bath medium in the second bath are respectively maintainable at two different temperatures;

a powder-removing device such that in operation, before an imaging, the powder-removing device mechanically removes particles of a powder adhering to the at least one reactor, wherein the powder is at least one of the bath media in use;

a transfer means for allowing the at least one reactor to be in the two baths in a plurality of thermal cycles to alternately attain:

a predetermined high target temperature $T_{HT}$, and a predetermined low target temperature $T_{LT}$;

a florescent imaging means for imaging the reaction material during or after the thermal cycling.

2. The apparatus according to claim 1, wherein the powder-removing device is provided above the two baths such that in operation the particles of the powder removed from the at least one reactor drop into the two baths.

3. The apparatus according to claim 1, further comprising:

a container, wherein in operation the particles of the powder removed from the at least one reactor are dropped into the container.

4. The apparatus according to claim 1, wherein operationally the powder-removing device executes a movement by an electromechanical means.

5. The apparatus according to claim 1, wherein the powder-removing device comprises an elastic surface for contacting the at least one reactor.

6. The apparatus according to claim 1, wherein the powder-removing device comprises bristles for contacting the at least one reactor.

7. The apparatus according to claim 6, wherein the bristles have a plurality of lengths.

8. The apparatus according to claim 1, wherein the powder-removing device comprises a fabric coated surface for contacting the at least one reactor.

9. The apparatus according to claim 1, wherein in operation, the powder-removing device provides an air jet for contacting the at least one reactor.

10. The apparatus according to claim 9, wherein in operation, the air jet is maintainable at a third predetermined temperature.

11. The apparatus according to claim 10, further comprising:

a container; and a guarding means to assist the particles of the powder removed from the at least one reactor to fall into the two baths or into the container.

12. The apparatus according to claim 1, wherein the powder-removing device comprises a first layer and a second layer in a stack, such that in operation the at least one reactor passes through both of the first layer and the second layer.

13. The apparatus according to claim 12, wherein the first layer and the second layer are horizontally in mutually orthogonal directions.

14. The apparatus according to claim 12, wherein the first layer comprises a plurality of first elastic flaps, the second layer comprises a plurality of second elastic flaps, and the first elastic flaps and the second elastic flaps are mutually misaligned along an axis vertical to the first layer and the second layer.

15. The apparatus according to claim 12, wherein
the first layer comprises first elastic bristles,
the second layer comprises second elastic bristles, and
the first elastic bristles and the second elastic bristles are
mutually misaligned along an axis vertical to the first layer and the second layer.

16. The apparatus according to claim 1, wherein the powder-removing device comprises a high temperature resistant surface for contacting the at least one reactor, and the high temperature resistant surface is configured to tolerate temperatures above 100 degrees Celsius.

17. The apparatus according to claim 1, wherein in use the powder-removing device is located on a top open side of at least one of the two baths such that the powder-removing device substantially covers the top open side, and enables the at least one reactor to be inserted through the powder-removing device into the bath media and taken out.

18. The apparatus according to claim 17, wherein
in use the powder-removing device covers the top open side securely enough to prevent the powder from spilling out when the at least one of the two baths is not held upright, and
the powder has a largest dimension of 5 millimeters.

19. The apparatus according to claim 1, wherein
the powder-removing device comprises a plurality of portions, wherein in operation the plurality of portions make a contact with the at least one reactor by clamping at least a portion of the at least one reactor, and
the contact is made only during or after lifting out the at least one reactor from the powder.

20. The apparatus according to claim 19, wherein a tightness of the clamping is adjustable.

\* \* \* \* \*